United States Patent [19]

Murachi et al.

[11] Patent Number: 4,778,754

[45] Date of Patent: Oct. 18, 1988

[54] REAGENT FOR DETERMINING THE AMOUNT OF MAGNESIUM IONS

[75] Inventors: Takashi Murachi, Kyoto; Katsuyoshi Tabata, Takatsuki, both of Japan

[73] Assignee: Unitika Ltd., Hyogo, Japan

[21] Appl. No.: 925,261

[22] Filed: Oct. 31, 1986

[30] Foreign Application Priority Data

Dec. 24, 1985 [JP] Japan ................................ 60-291484

[51] Int. Cl.$^4$ ............................................. C12Q 1/54
[52] U.S. Cl. .......................................... 435/14; 435/4; 435/15; 435/26
[58] Field of Search ..................................... 435/14, 15

[56] References Cited

U.S. PATENT DOCUMENTS 4,438,199 3/1984 Miwa et al. ............................. 435/26
4,657,854 4/1987 Wegfahrt ............................... 435/17

OTHER PUBLICATIONS

Analytical Biochemistry, vol. 18, pp. 270-273 (1967), "An Ultraspecific Micromethod for the Determination of D-Glucose" M. Y. Kamel et al.

*Primary Examiner*—Sam Rosen
*Attorney, Agent, or Firm*—Wenderoth, Lind & Ponack

[57] ABSTRACT

Disclosed is a reagent for determining the amount of magnesium ions, comprising glucokinase, adenosine-5'-triphosphate, glucose, glucose-6-phosphate dehydrogenase and oxidized-form nicotinamide adeninedinucleotide(phosphate), whereby the amount of magnesium ions can be accurately determined. The reagent is excellent in storage stability.

8 Claims, 2 Drawing Sheets

REAGENT FOR DETERMINING THE AMOUNT OF MAGNESIUM IONS

FIELD OF THE INVENTION

The present invention relates a reagent for determining the amount of magnesium ions.

BACKGROUND OF THE INVENTION

Determination of the amount of magnesium ions is generally classified into two methods; one is a physicochemical determination, especially an atomic-absorption spectrophotometry method, and the other is a chemical determination such as a method employing xylidyl blue. The physicochemical determination can give accurate results, but it needs an expensive analyzer and the operations of the analyzer are very complicated. The chemical determination can not give accurate results, because the specificity of reagents to be employed is so low that the reagents tend to react with other materials than magnesium ions.

In order to overcome the above mentioned problems, there is proposed a reagent for determining the amount of magnesium ions comprising hexokinase (HK) and glucose-6-phosphate dehydrogenase (G6PBH), in Methods of Enzymatic Analysis Third Edition, pages 529 to 597 (1985). The reagent utilizes a reaction system wherein the magnesium ions are essential for obtaining activity in the coupled reaction of hexokinase (HK) and glucose-6-phosphate dehydrogenase (G6PDH). The reaction mechanism is as follows:

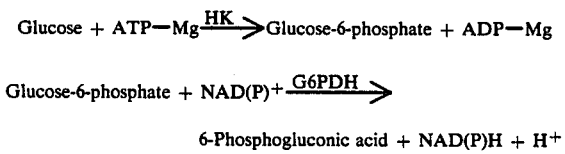

6-Phosphogluconic acid + NAD(P)H + H$^+$

Wherein ATP represents adenosine-5'-triphosphate, ADP represents adenosine-5'-diphosphate, and NAD(P)$^+$ represents oxidized-form nicotinamide adeninedinucleotide(phosphate). In the reaction mechanism, hexokinase (HK) does not exhibit activity to ATP until the magnesium ions are reacted with adenosine-5'-triphosphate (ATP) and changed to ATP-Mg, because ATP-Mg is a substrate of hexokinase (HK) but adenosine-5'-triphosphate (ATP) is not. Accordingly, in order to determine the amount of the magnesium ions, the concentration of adenosine-5'-triphosphate (ATP) must be adjusted to more than that of the magnesium ions. Otherwise, only a portion of magnesium ions is converted into ATP-Mg and the remaining magnesium ions do not take part in the above reaction mechanism.

On the other hand, hexokinase (HK) also has an adenosinetriphosphatase (ATP ase) activity by which adenosine-5'-triphosphate (ATP) is hydrolyzed into adenosine-5'-diphosphate (ADP) and thus, in the reaction mechanism, the concentration of adenosine-5'-triphosphate (ATP) tends to decrease by an attack of hexokinase (HK). As a result, it becomes difficult to adjust the concentration of adenosine-5'-triphosphate (ATP) to more than that of the magnesium ions. Accordingly, an accurate determination of the amount of magnesium ions is difficult.

Japanese Patent Publication (unexamined) 169598/1981 discloses a measuring composition comprising glucokinase (Glck) and glucose-6-phosphate dehydrogenase (G6PDH). The composition is employed for determining the amount of glucose or creatine kinase, but not for magnesium ions.

It has been found by the present inventors that glucokinase (Glck) indicates a high specificity to glucose but does not indicate an adenosinetriphosphatase (ATP ase) activity to adenosine-5'-triphosphate (ATP), and that, when the glucokinase (Glck) is coupled with glucose-6-phosphate dehydrogenase (G6PDH), magnesium ions can be accurately determined. There are no reports disclosing that the coupled reaction of glucokinase (Glck) and glucose-6-phosphate dehydrogenase (G6PHD) is utilized for determining the amount of magnesium ions.

SUMMARY OF THE INVENTION

The present invention is to provide a reagent for determining the amount of magnesium ions, comprising glucokinase, adenosinetriphosphate, glucose, glucose-6-phosphate dehydrogenase and oxidized-form nicotinamide adeninedinucleotide(hosphate) According to the present invention, the amount of magnesium ions can be accurately determined. The reagent of the present invention is excellent in storage stability and therefore it can be used for routine examinations

DETAILED DESCRIPTION OF THE INVENTION

Figure 1:
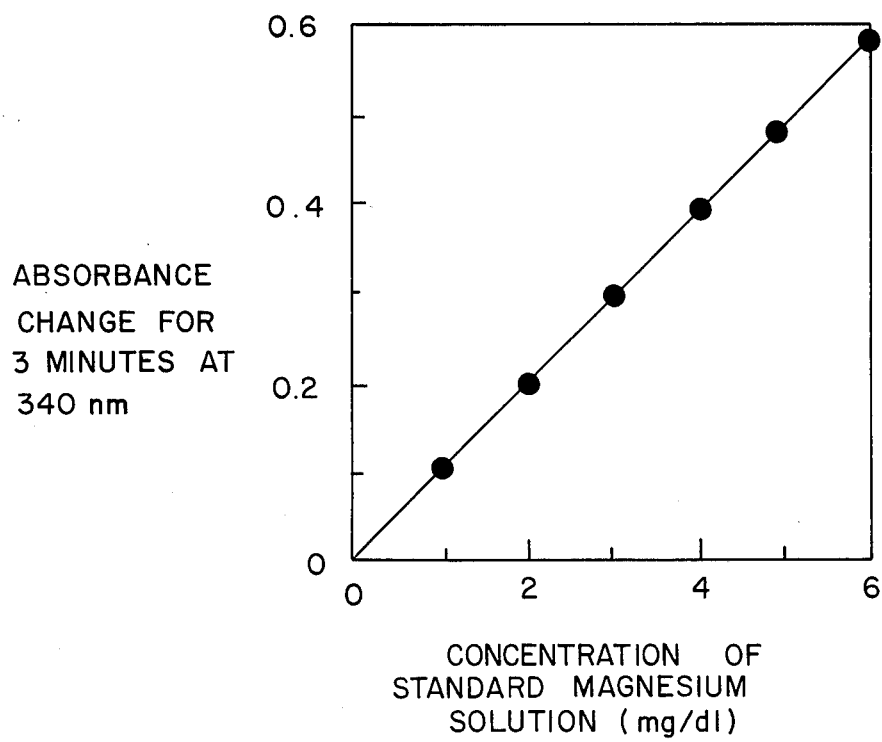
FIG. 1 and FIG. 2 are graphs showing the results of Example 1 and Comparative Example 1.

The glucokinase (Glck) employed in the present invention is not limited in its supply source and can be derived from said sources as microorganisms or animals. Preferred are those obtained from microorganisms at a most suitable growth temperature of 50° to 85° C. Examples of the microorganisms are Bacillus sp. such as *Bacillus stearothermophilus, Bacillus thermoproteolyticus, Bacillus acidocaldarius;* Thermoactinomyces sp.; Thermus sp.; Thermomicrobium sp. and the like. Typical examples of the microorganisms are *Bacillus stearothermophilus*, of which specific examples are ATCC 7933 strain (ATCC; The American Type Culture Collection, Maryland, U.S.A.), ATCC 7954 strain, ATCC 10194 strain, ATCC 12980 strain, NCA 1503 strain (NCA; National Canners Association, Washington, D.C., U.S.A.), UK 563 strain (FERM P-7275 strain, deposited at Fermentation Research Institute, Agent of Industrial Science and Technology, Ibaragi, Japan, on Sept. 29, 1983) and the like.

Glucose-6-phosphate dehydrogenase (G6PDH) is not limited in its supply sources, similar to that of glucokinase, and may be those which can act on nicotinamide adeninedinucleotidephosphate (NADP$^+$) and nicotinamide adeninedinucleotide (NAD$^+$) as a coenzyme. Preferred are those derived from *Leuconostoc mesenteroides* or *Pseudomonas fluorescens.* More preferred are those derived from thermophilic microorganisms, which can act on both nicotinamide adeninedinucleotide (NAD$^+$) and nicotinamide adeninedinucleotidephosphate (NADP$^+$) and which are excellent in stability.

The other components employed in the reagent of the present invention are known. For example, glucose, adenosinetriphosphate (ATP) and oxidized-form nicotinamide adeninedinucleotide(phosphate) are obtained from Sigma Chemical Co.

The reagents of the present invention can be prepared by adding the components mentioned above to a buffer solution having a pH of 5 to 10. The buffer solution may be a Tris-hydrochloric acid solution, triethanolaminehydrochloric acid solution, imidazolehydrochloric acid solution, tris(hydroxymethyl)methylglycine solution or N,N-bis(2-hydroxyethyl)glycine solution. The amount of the buffer solution may be 10 to 500 mM. The reagents of the present invention may further contain other additives. Examples of the additives are thiol compounds such as N-acetylcystein, glutathion, 2-aminoethanol, dithiothreitol, dithioerythritol and the like, sodium azide as antiseptics and the like. Examples of the stabilizers are proteins such as albumin, gamma-globulin and the like; water-soluble polymer compounds such as polyvinyl alcohol, polyethylene glycol and the like. The amount of the additives are 0.1 to 100 mM.

The amounts of the components to be introduced are not limited. The amount of oxidized form nicotinamide adeninedinucleotide(phosphate) (NAD(P)+) is typically from 0.02 to 10 mM, preferably from 0.1 to 5 mM. The amount of glucose is generally from 1 to 100 mM, preferably 5 to 50 mM. Adenosinetriphosphate (ATP) may be employed in an amount of 0.05 to 5 mM, preferably 0.1 to 3 mM. Glucokinase (Glck) may be employed in an amount of 0.01 to 10 μ/ml, preferably 0.05 to 5 μ/ml. The amount of glucose-6-phosphate (G6PDH) is generally from 0.01 to 10 μ/ml, preferably 0.05 to 5 μ/ml.

The reagents of the present invention can be used as a one-reagent or two-reagent type. Preferably, the reagents are divided into two types, for example, the first reagent includes glucose, oxidized-form nicotinamide adeninedinucleotide(phosphate) (NAD(P)+) and adenosine-5'-triphosphate (ATP) and the second reagent includes glucokinase (Glck) and glucose-6-phosphate dehydrogenase (G6PDH). The latter reagent can be mixed together before a determination. The volume ratio of the first reagent to the second reagent is within the range of 1:1 to 6:1.

According to the present invention, a determination of magnesium ions can be carried out, for example, by mixing the first reagent of the present reagent with a sample, maintaining for about 3 minutes at a temperature of 20° to 50° C., put it into a cuvette in a spectrophotometer to which the second reagent is added and mixed, and then determining absorbance at 340 nm. A reaction time after adding the second reagent may be 1 to 30 minutes, preferably 2 to 5 minutes for an analyzer.

The reaction mechanism of the present invention is believed as follows:

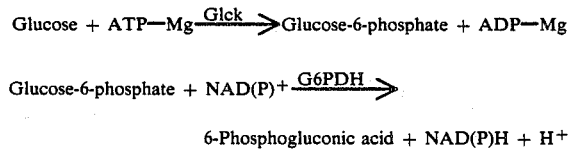

The present invention is illustrated by the following examples, which are not to be construed as limiting the invention to their details.

EXAMPLE 1 AND COMPARATIVE EXAMPLE 1

A first reagent was prepared from 1 mM of adenosinetriphosphate (ATP), 0.5 mM of oxidation-type nicotinamide adeninedinucleotidephosphate (NADP+), 30 mM of glucose and 50 mM of a Tris-hydrochloric acid solution (pH8.5). A second reagent was prepared from 0.65 μ/ml of glucokinase (Glck) derived from *Bacillus stearothermophilus* available from Seikagaku Kogyo K.K.) and 0.65 μ/ml of glucose-6-phosphate (G6PDH) derived from *Leuconostoc mesenteroides* (available from Oriental Yeast K.K.).

Six samples containing magnesium ions and one blank were determined by the reagent prepared above. The concentrations of magnesium ions in the six samples were 1, 2, 3, 4, 5 and 6 mg/dl, respectively. Distilled water was used for blank test. The first reagent of 2.4 ml was mixed with 0.01 ml of each sample and allowed to stand at 30° C. for 3 minutes. The second reagent of 0.6 ml was then mixed with the resultant mixture to determine a change in absprbance at 340 nm for 3 minutes in a cuvette having a light path of 1 cm. A relation of the magnesium concentrations to the determined absorbance changes was plotted in FIG. 1. As is apparent from FIG. 1, when a magnesium concentration was 6 mg/dl, the determined absorbance change was about 0.6 and, at the other points, the relation was same.

For a comparison, an experiment was performed as generally described above, with the exception that hexokinase (HK) derived from Baker's yeast (available from Oriental Yeast K.K.) was employed instead of glucokinase (Glck). The result was shown in FIG. 2. As is apparent from FIG. 2, when a magnesium concentration was 6 mg/dl, the determined absorbance change was less than 0.4.

Figure 2:
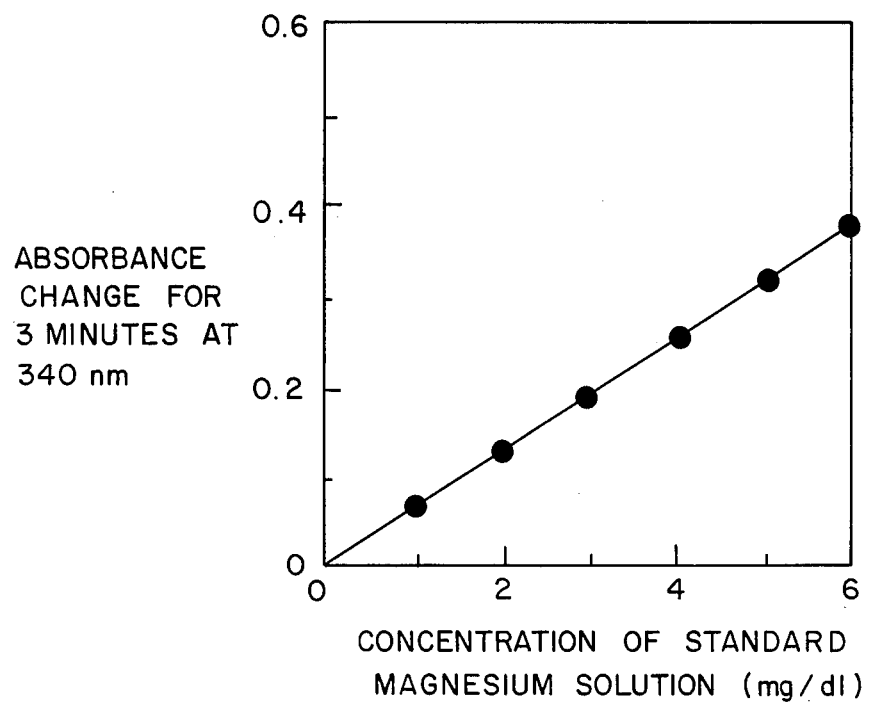

The difference of the absorbance changes between FIGS. 1 and 2 indicates the difference of the sensitivity of determination and accordingly the reagent of the present invention is nealy double high in sensitivity.

Further, the reagents thus obtained were allowed to stand in a refrigerator for a certain time to check stability. The reagent of the present invention maintained the same sensitivity as FIG. 1 even after 30 days. On the other hand, the sensitivity of the reagent made for the comparison reduced to less than half of the sensitivity of FIG. 2 in two days.

What is claimed is:

1. A reagent for determining the amount of magnesium ions, comprising effective amounts for determining magnesium ions, of glucokinase, adenosine-5'-triphosphate, glucose, glucose-6-phosphate dehydrogenase and oxidized-form nicotinamide adeninedinucleotide phosphate.

2. The reagent according to claim 1 wherein glucokinase is derived from microorganisms.

3. The reagent according to claim 2 wherein the microorganism is *Bacillus stearothermophilus*.

4. The reagent according to claim 1 wherein glucose-6-phosphate dehydrogenase is derived from *Leuconostoc mesenteroides*.

5. The reagent according to claim 1 wherein the reagent is divided into two reagents, in which the first reagent comprises glucose, oxidized-form nicotinamide adeninedinucleotide(phosphate) and adenosine-5'-triphosphate and the second reagent comprises glucokinase and glucose-6-phosphatedehydrogenase.

6. The reagent according to claim 5 wherein the volume ratio of the first reagent to the second reagent is within the range of 1:1 to 6:1.

7. The reagent according to claim 1 wherein the reagent is divided into two reagents, in which the first reagent comprises glucose, oxidized-form nicotinamide adeninedinucleotide(phosphate), glucokinase and glucose-6-phosphate dehydrogenase and the second reagent comprises adenosine-5'-triphosphate.

8. The reagent according to claim 1 wherein the reagent is divided into two reagents, in which the first reagent comprises oxidized-form nicotinamide adeninedinucleotide(phosphate), adenosine-5'-triphosphate, glucokinase and glucose-6-phosphate dehydrogenase and the second reagent comprises glucose.

* * * * *